United States Patent
Ohtsuka et al.

(10) Patent No.: US 6,207,837 B1
(45) Date of Patent: Mar. 27, 2001

(54) PROCESS FOR PRODUCING DIBENZO[B,F] THIEPINE DERIVATIVES

(75) Inventors: Naomi Ohtsuka; Shuji Jinno; Takaaki Okita, all of Tokyo (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 0 days.

(21) Appl. No.: 09/462,903

(22) PCT Filed: Jul. 13, 1998

(86) PCT No.: PCT/JP98/03129
§ 371 Date: Jan. 18, 2000
§ 102(e) Date: Jan. 18, 2000

(87) PCT Pub. No.: WO99/03827
PCT Pub. Date: Jan. 28, 1999

(30) Foreign Application Priority Data

Jul. 18, 1997 (JP) .................................................. 9-193646

(51) Int. Cl.$^7$ .................... C07D 337/12; C07C 225/00; C07C 321/00; C07C 331/00
(52) U.S. Cl. .......................... 549/12; 558/410; 562/432; 568/74; 568/75
(58) Field of Search .............................. 549/12; 558/410; 562/432; 568/74, 75

(56) References Cited

U.S. PATENT DOCUMENTS

| | | | |
|---|---|---|---|
| 4,605,713 | 8/1986 | Heitz et al. | 525/537 |
| 5,405,969 | 4/1995 | Wright et al. | 548/250 |
| 6,060,468 | * 5/2000 | Jorgensen et al. | 514/218 |
| 6,111,115 | * 8/2000 | Yamamoto et al. | 549/12 |

FOREIGN PATENT DOCUMENTS

| | | |
|---|---|---|
| 61-7249 | 1/1986 | (JP) . |
| 2-262554 | 10/1990 | (JP) . |
| 7-224028 | 8/1995 | (JP) . |
| 8-99953 | 4/1996 | (JP) . |
| 97/25985 | 7/1997 | (WO) . |

OTHER PUBLICATIONS

C. Hamdouchi et al., "A Novel Application of the Ullmann Coupling Reaction for the Alkylsulfenylation of 2–Amino–Imidazo[1,2–α]pyridine", Tetrahedron, 55, (1999), pp. 541–548.

* cited by examiner

*Primary Examiner*—Deborah C. Lambkin
(74) *Attorney, Agent, or Firm*—Wenderoth, Lind & Ponack, L.L.P.

(57) ABSTRACT

Efficient synthesis of diaryl sulfide derivatives useful as intermediates for pharmaceutical compounds. Provision of a convenient process for producing large quantities of dibenzo [b,f]thiepine derivatives using such intermediates.

Halogen-substituted phenyl derivatives of the general formula (1):

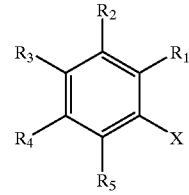

(1)

(where X is a halogen atom and $R_1$–$R_5$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group) are reacted with disulfide derivatives of the general formula (2):

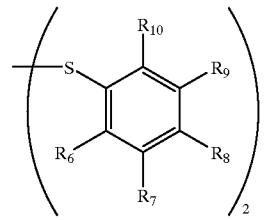

(2)

(where $R_6$–$R_{10}$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group) in the presence of metal catalysts to form a sulfide bond, thereby producing diaryl sulfide derivatives of the general formula (3):

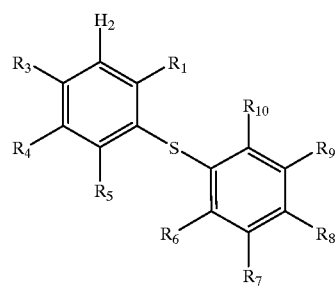

(3)

(where $R_1$–$R_{10}$ are the same as defined above) or salts thereof. Pharmaceutical compounds such as dibenzo[b,f] thiepine derivatives are produced from the diaryl sulfide derivatives or salts thereof by known techniques.

9 Claims, No Drawings

PROCESS FOR PRODUCING DIBENZO[B,F] THIEPINE DERIVATIVES

This application is a 371 of PCT/JP 98/03129 Jul. 13, 1988.

TECHNICAL FIELD

This invention relates to a process for producing diaryl sulfide derivatives or salts thereof which are intermediates of pharmaceutical compounds. The invention also relates to a process for producing dibenzo[b,f]thiepine derivatives using such intermediates.

BACKGROUND ART

Symmetric and asymmetric diaryl sulfide derivatives are compounds useful as intermediates in the production of many pharmaceutical compounds. For example, bis(3,5-dimethoxy-phenyl)disulfide which is a symmetric diaryl sulfide derivative is a compound useful as an intermediate for the synthesis of dibenzo[b,f]thiepine derivatives. Methods of synthesizing dibenzo[b,f]thiepine derivatives from bis(3,5-dimethoxyphenyl)disulfide have already been described in Japanese Patent Application No. 7904/1996 (International Publication WO97/25985) and so forth.

Compounds bearing a dibenzo[b,f]thiepine skeleton are known to include compounds having a broad range of pharmacological activities such as an anti-inflammatory action [Chemical and Pharmaceutical Bulletin 36, 3462 (1988)], an antispasmodic action (Japanese Patent Public Disclosure No. 160288/1975), an antiestrogenic action [Journal of Medicinal Chemistry 26, 1131 (1983)], an anti-oxidative action (International Patent Application No. 96/10021), a cerebral function improving action (International Patent Application No. 96/25927), and a trachea dilating action (Japanese Patent Application No. 7904/1996, or International Publication WO97/25985). For effective utilization of these pharmacological activities, a method capable of efficient massive supply of compounds having the dibenzo[b,f]thiepine skeleton is desired.

DISCLOSURE OF INVENTION

The present invention purports to realize efficient synthesis of diaryl sulfide derivatives useful as intermediates of pharmaceutical compounds and to provide a convenient process for producing large volumes of dibenzo[b,f]thiepine derivatives using such intermediates.

In order to realize massive and convenient production of dibenzo[b,f]thiepine derivatives, the present inventors conducted various experiments on various starting materials, reactions and intermediates and found that thiol derivatives, among other things, reacted with halogen-substituted phenyl derivatives via the intermediate disulfide derivatives to produce diaryl sulfide derivatives. Based on these findings, the inventors continued the intensive research and finally accomplished the present invention, which relates to a process for producing diaryl sulfide derivatives or salts thereof comprising reacting halogen-substituted phenyl derivatives with disulfide derivatives in the presence of metal catalysts to produce symmetric or asymmetric diaryl sulfide derivatives, as well as a process for producing dibenzo[b,f]thiepine derivatives by known techniques using said symmetric or asymmetric diaryl sulfide derivatives.

Thus, the present invention in essence relates to a process for producing diaryl sulfide derivatives or salts thereof by reacting halogen-substituted phenyl derivatives of the general formula (1):

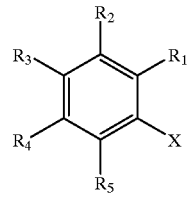

(1)

(where X is a halogen atom and $R_1$–$R_5$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group) with disulfide derivatives of the general formula (2):

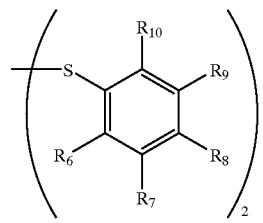

(2)

(where $R_6$–$R_{10}$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group) in the presence of metal catalysts to form a sulfide bond, thereby producing diaryl sulfide derivatives of the general formula (3):

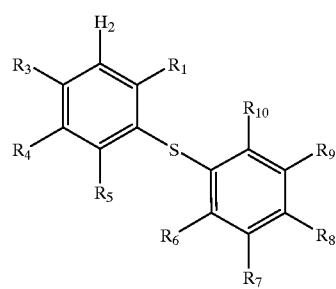

(3)

(where $R_1$–$R_{10}$ are the same as defined above). The end compound diaryl sulfide derivatives or salts thereof are intermediates of pharmaceutical compounds, preferably dibenzo[b,f]thiepine derivatives. The salts of the general formula (3) include alkali metal salts such as sodium salt, potassium salt and lithium salt, alkaline earth metal salts such as calcium salt and magnesium salt, and organic amine addition salts such as ammonium salt, triethylamine and piperidine.

The disulfide derivatives of the general formula (2) to be used in the invention are preferably compounds that are produced by oxidizing thiol derivatives of the general formula (4) as a starting material:

(4)

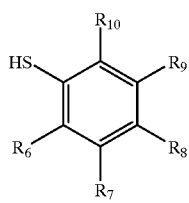

(where $R_6$–$R_{10}$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group). The disulfide derivatives of the general formula (2) to be used in the invention may also be intermediates that are produced within the reaction system starting from the thiol derivatives of the general formula (4).

The present invention preferably relates to a process by which the desired diaryl sulfide derivatives or salts thereof are produced as intermediates for pharmaceutical compounds such as dibenzo[b,f]thiepine derivatives. The present invention adopts known techniques for converting the intermediate diaryl sulfide derivatives or salts thereof into pharmaceutical compounds such as dibenzo[b,f]thiepine derivatives. Preferred examples of the dibenzo[b,f]thiepine derivatives include 7,9-dimethoxy-10,11-dihydrodibenzo[b,f]thiepin-10-one of the formula (5):

(5)

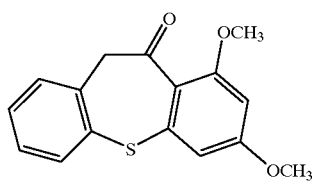

7,9-dihydroxy-10,11-dihydrodibenzo[b,f]thiepin-10-one of the formula (6):

(6)

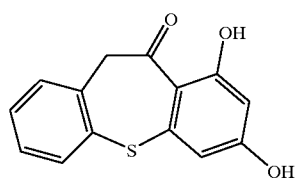

and 10,11-dihydrodibenzo[b,f]thiepin-1,3-diol of the formula (7):

(7)

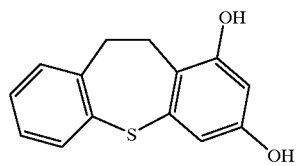

The present invention also relates in essence to a process comprising the steps of reacting halogen-substituted phenyl derivatives with disulfide derivatives in the presence of metal catalysts to produce diaryl sulfide derivatives and applying known techniques to the obtained diaryl sulfide derivatives to produce the above-listed dibenzo[b,f]thiepine derivatives. More specifically, the invention relates in essence to a process for producing diaryl sulfide derivatives or salts thereof by the steps of:

reacting a 2-halobenzoic acid of the general formula (8):

(8)

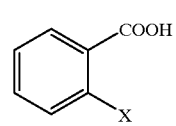

(where X is a halogen atom) with bis(3,5-dimethoxyphenyl)-disulfide of the formula (9):

(9)

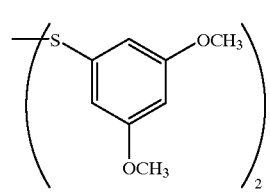

in the presence of a metal catalyst to form a sulfide bond, thereby producing 2-(3,5-dimethoxyphenylthio) benzoic acid of the formula (10):

(10)

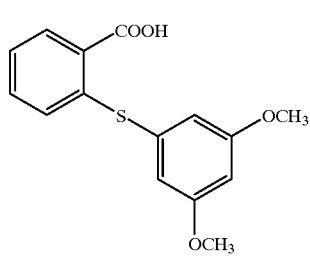

then reducing the compound (10) to form an alcohol derivative of the formula (11):

(11)

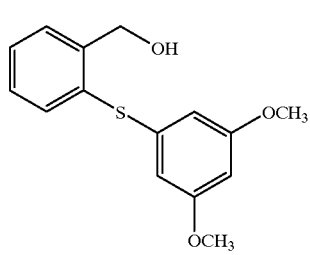

reacting the compound (11) with a halogenating agent or a pseudo-halogenating agent to produce a halogen derivative of the general formula (12):

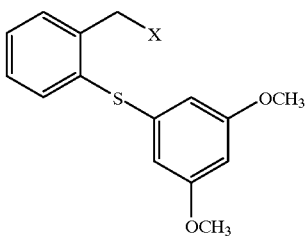

(12)

(where X is a halogen atom or a pseudo-halogen leaving group);

reacting the compound (12) with a nitrile forming agent to produce a nitrile derivative, or 2-(3,5-dimethoxyphenyl-thio)benzylnitrile of the formula (13):

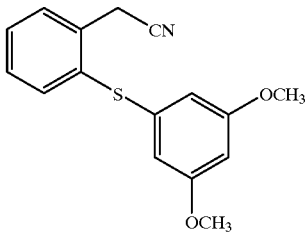

(13)

hydrolyzing the compound (13) to generate a carboxylic acid derivative; and cyclizing this derivative by an intramolecular Friedel-Crafts reaction to yield 7,9-dimethoxy-10,11-dihydrodibenzo-[b,f]thiepin-10-one of the formula (5):

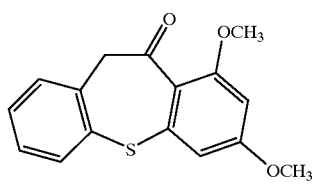

(5)

The invention further relates in essence to a process for producing diaryl sulfide derivatives or salts thereof in which the cyclized 7,9-dimethoxy-10,11-dihydrodibenzo[b,f]thiepin-10-one of the formula (5) is deprotected to yield a diol form, or 7,9-dihydroxy-10,11-dihydrodibenzo[b,f]thiepin-10-one of the formula (6):

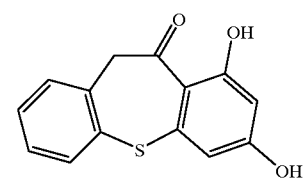

(6)

The invention further relates in essence to a process for producing diaryl sulfide derivatives or salts thereof in which 7,9-dihydroxy-10,11-dihydrodibenzo[b,f]thiepin-10-one which is the diol compound of the formula (6) or 7,9-dimethoxy-10,11-dihydrodibenzo[b,f]thiepin-10-one which is the dimethoxy compound of the formula (5) is reduced and deprotected to yield 10,11-dihydrodibenzo[b,f]thiepin-1,3-diol of the formula (7):

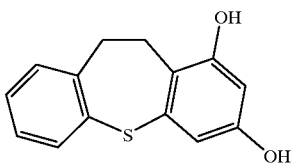

(7)

The starting compounds embraced within the general formulas (1), (2) and (4) are either commercial products or readily available by implementing the methods described in the examples of the invention and literature [Journal of Organic Chemistry 34, 1463, (1969)] or modifications thereof. The compounds embraced within the general formula (3) are obtained in high yields by heating mixtures of starting compounds embraced within the general formula (1), starting compounds embraced within the general formula (2), metal catalysts and solvents.

The metal catalysts to be used in the process described above are not limited to any particular types as long as they contribute to the progress of the reaction involved and copper catalysts and nickel catalysts may be mentioned as preferred examples. The solvents that can be used include dimethylformamide, dimethyl sulfoxide, hexamethylphosphoric triamide, N-methyl-2-pyrrolidone and amyl alcohol.

Bases that are necessary in the common Ullmann reaction are not essential to the progress of the reaction in the process of the invention. The reaction is complete at 80–120° C. in 0.5–24 hours, typically in 1–5 hours. The compounds obtained by the process described above and which are embraced within the general formula (3) can be isolated and purified by subjecting them to ordinary purification procedures commonly employed in organic synthetic chemistry, as exemplified by neutralization, filtration, extraction, washing, drying, concentrating, recrystallization and various types of chromatography.

Methods of synthesizing derivatives using the diaryl sulfide derivatives or salts thereof which are the pharmaceutical intermediates of the invention have already been described in Japanese Patent Application No. 7904/1996 (International Patent Publication WO97/25985) and so forth.

With respect to the method of synthesizing dibenzo[b,f]thiepin derivatives from bis(3,5-dimethoxy-phenyl) disulfide, documented techniques such as the one described in the patent publication mentioned above may be applied such that 2-halobenzoic acid of the general formula (8) is reacted with bis(3,5-dimethoxyphenyl)disulfide of the formula (9) to give 2-(3,5-dimethoxyphenylthio)benzoic acid of the formula (10), which is thereafter reduced with a metal hydride such as lithium aluminum hydride or diborane, halogen-substituted as by thionyl chloride or phosphorus tribromide, and converted to a nitrile compound as by treatment with sodium cyanide or potassium cyanide, thereby yielding 2-(3,5-dimethoxy-phenylthio)benzylnitrile [(formula (13)]. This compound is hydrolyzed with a base or an acid and cyclized by an intramolecular Friedel-Crafts reaction typically using methanesulfonic acid or polyphosphoric acid, thereby producing a tricyclic compound, or 7,9-dimethoxy-10,11-dihydrodibenzo[b,f]thiepin-10-one

[formula (5)], which is then deprotected with pyridine hydrochloride, boron tribromide or the like to yield 7,9-dihydroxy-10,11-dihydrodibenzo[b,f]thiepin-10-one [formula (6)].

Further, the ketone group in 7,9-dihydroxy-10,11-dihydrodibenzo[b,f]thiepin-10-one of the formula (6) is removed by reduction to yield 10,11-dihydrodibenzo[b,f]-thiepin-1,3-diol [(formula (7)].

The thus produced compounds [formulas (6) and (7)] exhibit physiological activities such as an antioxidative action, an anti-inflammatory action, a cerebral function improving action and a bronchodilating action.

The synthesis of symmetric and asymmetric diaryl sulfide derivatives generally involve a reaction called the Ullmann reaction [Tetrahedron 26, 113 (1983)]. In the Ullmann reaction, an arylthiol is reacted with an arylhalogen compound in the presence of a copper catalyst and a base to produce a symmetric or asymmetric diaryl sulfide derivative. In this reaction, the base in the system first converts the arylthiol to an aryl thiolate. Without this conversion, the reaction yield drops. In this reaction system, disulfides are by-products and have been considered to be a cause of low yield [Chemical and Pharmaceutical Bulletin 26, 3058 (1978)]. Hence, anyone who wants to utilize the Ullmann reaction has thought it impossible to use substrates that are labile to bases. In addition, if thiol derivatives that readily undergo oxidation to form disulfides are used, it is difficult to establish the appropriate reaction conditions and only low yield results.

In the reaction involved in the present invention, the reaction intermediate is a disulfide and, hence, bases are essentially unnecessary. If thiol is used as a starting material, a dimerized disulfide also occurs during the reaction. Therefore, the method of the invention is also applicable to substrates that are labile to bases and which have not heretofore been used. The reaction also proceeds in high yields with thiol derivatives such as 3,5-dimethoxy-thiophenol that easily undergo oxidation to give disulfides. Another great advantage of the invention is its ability to use more stable disulfides as a feed material. In addition, by applying the method of the invention, dibenzo[b,f]thiepine derivatives having antioxidative, anti-inflammatory, cerebral function improving and bronchodilating actions can be synthesized from the diaryl sulfide derivatives of the general formula (3).

As will be shown in the examples to be described later, the synthesis of intermediates for dibenzo[b,f]thiepines that has heretofore been possible only in a low yield in the prior art method can be markedly improved by the present invention.

BEST MODE FOR CARRYING OUT THE INVENTION

Details of the invention are given below with reference to examples. It should be noted that the invention is in no way limited by those examples.

EXAMPLE 1

Synthesis of 2-(3,5-dimethoxyphenylthio)benzoic acid [formula (10)]

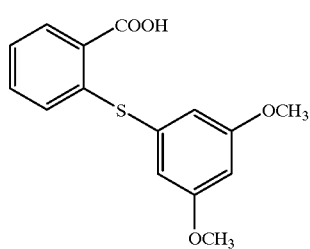

Stage 1

Synthesis of bis(3,5-dimethoxyphenyl)disulfide [formula (9)]

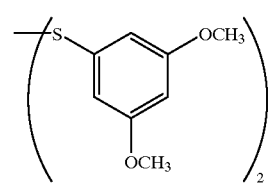

To a suspension of 3,5-dimethoxyaniline (7.5 g) in 40 ml of water was added conc. hydrochloric acid (12 N, 10.0 ml) to form a hydrochloride and the suspension was cooled on an ice bath. With the reaction temperature held below 5° C., 3.3 g of sodium sulfite dissolved in water (10.2 ml) was added carefully and the resulting mixture was stirred for 30 minutes (to prepare solution 1).

A mixture of potassium xanthogenate (50.7 g) suspended in water (40 ml) was heated to 85–90° C. so that it dissolved completely (to prepare solution 2).

To solution 2 being stirred at the same temperature, solution 1 was slowly added over 30 minutes and the mixture was stirred for another 30 minutes. On cooling, the mixture was extracted three times with ethyl acetate and washed with 1 N sodium hydroxide, water and brine. After drying the organic layer over anhydrous sodium sulfate, the solvent was removed under reduced pressure to give a xanthate. To the ester, dissolved in 36 ml of ethanol and 4 ml of water, was added 20.0 g of potassium hydroxide and the mixture was stirred under reflux for 6 hours. On cooling, the mixture was treated with 2.0 g of copper (II) oxide (powder) and stirred at room temperature for 3 hours while being bubbled with oxygen (or air). The insoluble materials were removed by filtration, the ethanol was evaporated under reduced pressure and water was added. The aqueous layer was extracted three times with ethyl acetate and washed successively with 1 N hydrochloric acid, water and brine. The ethyl acetate layer was dried over anhydrous sodium sulfate, concentrated, and then purified by column chromatography (eluting solvent; hexane:ethyl acetate=7:1) to give 3.18 g (40%) of a compound of the indicated formula (9).

Stage 2

Synthesis of 2-(3,5-dimethoxyphenylthio)benzoic acid [(formula (10)]

A mixture of 2-bromobenzoic acid (16 g), bis(3,5-dimethoxyphenyl)disulfide of formula (9) (11.0 g), copper (II) oxide (6.5 g) and N-methyl-2-pyrrolidone (50 ml) was stirred at 200° C. for 1 hour. The reaction mixture was left to cool and adjusted to pH 2 with 4 N hydrochloric acid. The mixture was extracted with ethyl acetate and washed successively with water and brine. The organic layer was dried over anhydrous sodium sulfate, concentrated and then purified by silica gel column chromatography (eluting solvent; chloroform:methanol=97:3, 0.1% acetic acid) to give 12.3 g (65%) of a compound of the indicated formula (10). The compound had a melting point of 182° C.

EXAMPLE 2
Synthesis of 2-(3,5-dimethoxyphenylthio)benzoic acid [formula (10)]

A mixture of thiosalicylic acid (928.1 mg), 5-chloro-1,3-dimethoxybenzene (1.139 g), copper (powder) (222.4 mg), copper(I) iodide (666.6 mg) and N-methyl-2-pyrrolidone (5 ml) was stirred at 200° C. for 5 hours. After cooling, the reaction mixture was adjusted to pH 2 with 4 N hydrochloric acid, extracted with ethyl acetate and washed successively with water and brine. The organic layer was dried over anhydrous sodium sulfate, concentrated and then purified by silica gel column chromatography (eluting solvent; chloroform:methanol=97:3, 0.1% acetic acid) to give 397.6 mg (23%) of a compound of the indicated formula (10). The compound had a melting point of 182° C.

EXAMPLE 3
Synthesis of 2-(3,5-dimethoxyphenylthio)benzoic acid [(formula (10)]

A mixture of 2-bromobenzoic acid (40.2 mg), 3,5-dimethoxythiophenol (34.0 mg), copper (powder) (6.4 mg), copper(I) iodide (19.5 mg) and N-methyl-2-pyrrolidone (2 ml) was stirred at 170° C. for 30 minutes. The reaction mixture was treated by the same procedure as in Example 2 to give 24.5 mg (42%) of a compound of the indicated formula (10). The compound had a melting point of 182° C.

EXAMPLE 4
Synthesis of 2-(3,5-dimethoxyphenylthio)benzoic acid [formula (10)]

A mixture of 2-bromobenzoic acid (105.5 mg), bis(3,5-dimethoxyphenyl)disulfide [formula (9)] (71.0 mg), zinc (powder) (6.8 mg), bis(triphenylphosphine)nickel(II) dichloride (171.6 mg) and N-methyl-2-pyrrolidone (4 ml) was stirred at 150° C. for 4 hours. The reaction mixture was treated by the same procedure as in Example 2 to give 55.3 mg (45%) of a compound of the indicated formula (10). The compound had a melting point of 182° C.

EXAMPLE 5
Synthesis of 2-phenylthiobenzoic acid [formula (14)]

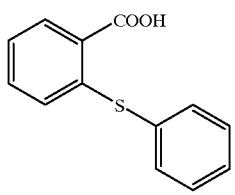

(14)

A mixture of 2-bromobenzoic acid (241.2 mg), diphenyl disulfide (109.2 mg), copper (powder) (31.8 mg), copper(I) iodide (95.2 mg) and N-methyl-2-pyrrolidone (10 ml) was stirred at 200° C. for 1 hour. The reaction mixture was left to cool and adjusted to pH 2 with 4 N hydrochloric acid. The mixture was extracted with ethyl acetate and successively washed with water and brine. After drying over anhydrous sodium sulfate, the solvent was removed under reduced pressure and the resulting crude product was purified by silica gel column chromatography (eluting solvent; hexane-:ethyl acetate=1:1) and recrystallized from ethyl acetate to give 150.0 mg (65%) of a compound of the indicated formula (14). The compound had a melting point of 178–180° C.

EXAMPLE 6
Synthesis of 2-phenylthiobenzoic acid [formula (14)]

A mixture of 2-bromobenzoic acid (40.2 mg), thiophenol (22.0 mg), copper (powder) (6.3 mg), copper (I) iodide (19.0 mg) and N-methyl-2-pyrrolidone (2 ml) was stirred at 200° C. for 1 hour. The reaction mixture was treated by the same procedure as in Example 4 to give 17.4 mg (38%) of a compound of the indicated formula (14). The compound had a melting point of 178–180° C.

EXAMPLE 7
Synthesis of 5-(3,5-dimethoxyphenylthio)-2-chlorophenylacetic acid [formula (15)]

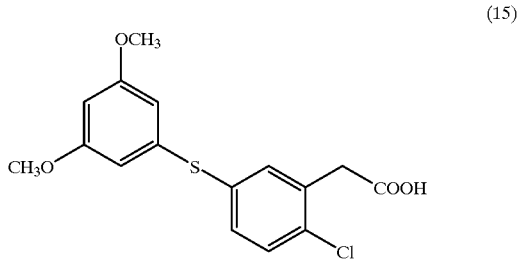

(15)

A mixture of 5-bromo-2-chlorophenylacetic acid (299.3 mg), bis(3,5-dimethoxyphenyl)disulfide of formula (9) (169.2 mg), copper(II) oxide (39.8 mg) and N-methyl-2-pyrrolidone (10 ml) was stirred at 170° C. for 1.5 hours. On cooling, the reaction mixture was adjusted to pH 2 with 4 N hydrochloric acid. The mixture was extracted with ethyl acetate and washed with water and brine, successively. The organic layer was dried over anhydrous sodium sulfate and the solvent was evaporated under reduced pressure. The residue was purified by silica gel column chromatography (eluting solvent; hexane:ethyl acetate=10:1) to afford 80.7 mg (21%) of a compound of the indicated formula (15). Its mass spectrum showed a mass number of 338 ($M^+$).

This compound gave the following peaks in $^1$H-NMR (400 MHz, $CDCl_3$).

δ (ppm)

3.73 (6H, s, $OCH_3$)

3.76–3.80 (2H, s, $Ar-CH_2$)

6.35 (1H, t, J=2Hz, Ar-H)

6.46 (2H, d, J=2Hz, Ar-H)

7.22 (1H, dd, J=2, 8Hz, Ar-H)

7.26–7.33 (2H, m, Ar-H)

EXAMPLE 8
Synthesis of 7,9-dimethoxy-10,11-dihydrodibenzo[b,f]thiepin-10-one [formula (5)]

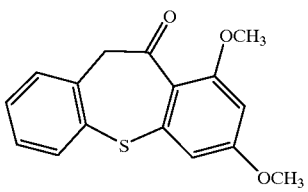

(5)

Stage 1
Synthesis of 2-(3,5-dimethoxyphenylthio)benzyl alcohol [formula (11)]

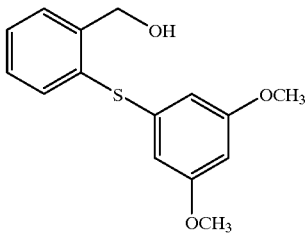

(11)

To a stirred solution of 12.3 g of the 2-(3,5-dimethoxyphenylthio)benzoic acid, prepared in Example 1, in 50 ml of anhydrous tetrahydrofuran was added 1.8 g of sodium borohydride portionwise at 0° C. After 30 minutes, the resulting solution was treated with 6.3 ml of $BF_3 \cdot Et_2O$ at the same temperature and then the mixture was stirred at room temperature for 1 hour. The reaction mixture was partitioned between ethyl acetate and dilute hydrochloric acid, and the ethyl acetate layer was successively washed with water and brine. The organic layer was dried over anhydrous sodium sulfate and concentrated. The concentrate was purified by silica gel column chromatography (eluting solvent; hexane:ethyl acetate=3:1) to give 8.3 g (71%) of a compound of the indicated formula (11).

This compound gave the following peaks in $^1$H-NMR (90 MHz, $CDCl_3$).

δ (ppm)
3.71 (6H, s, $OCH_3$)
4.78 (2H, s, Ar-$CH_2$)
6.2–6.5 (3H, m, Ar-H)
7.3–7.5 (4H, m, Ar-H)

Stage 2
Synthesis of 2-(3,5-dimethoxyphenylthio)benzyl bromide [formula (16)]

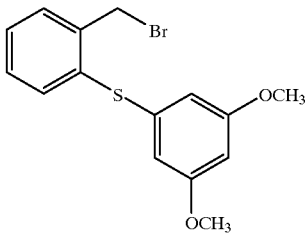

(16)

To a stirred solution of 2-(3,5-dmethoxyphenylthio) benzyl alcohol (8.3 g) in methylene chloride (18 ml) was added phosphorus tribromide (1 ml) at 0° C. and the mixture was stirred at the same temperature for 1 hour. After diluting with ethyl acetate, the solution was washed with water and brine and dried over anhydrous magnesium sulfate and the solvent was evaporated under reduced pressure. The residue was purified by silica gel column chromatography (eluting solvent; hexane:ethyl acetate=5:1) to give 8.0 g (79%) of a compound of the indicated formula (16).

This compound gave the following peaks in $^1$H-NMR (90 MHz, $CDCl_3$).

δ (ppm)
3.73 (6H, s, $OCH_3$)
4.70 (2H, s, Ar-$CH_2$)
6.3–6.4 (3H, m, Ar-H)
7.2–7.5 (4H, m, Ar-H)

Stage 3
synthesis of 2-(3,5-dimethoxyphenylthio)benzyl nitrile [formula (13)]

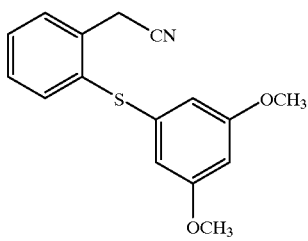

(13)

To a solution of 2-(3,5-Dimethoxyphenylthio)benzyl bromide (8.0 g) in dimethyl sulfoxide (50 ml) was added sodium cyanide (1.7 g) and the mixture was stirred at 80° C. for 1.5 hours. The reaction mixture was diluted with ethyl acetate, washed with water and brine, dried over anhydrous magnesium sulfate and the solvent was evaporated under reduced pressure. The residue was purified by silica gel column chromatography (eluting solvent; hexane:ethyl acetate=3:1) to give 5.9 g (88%) of a compound of the indicated formula (13).

This compound gave the following peaks in $^1$H-NMR (90 MHz, $CDCl_3$).

δ (ppm)
3.72 (6H, s, $OCH_3$)
3.87 (2H, s, Ar-$CH_2$)
6.2–6.5 (3H, m, Ar-H)
7.3–7.7 (4H, m, Ar-H)

Stage 4
Synthesis of 7,9-dimethoxy-10,11-dihydrodibenzo[b,f] thiepin-10-one [formula (5)]

To 2-(3,5-dimethoxyphenylthio)benzyl nitrile (5.9 g), ethanol (15 ml) and THF (7.5 ml) were added and dissolved; after the addition of 11 N aqueous sodium hydroxide (9 ml), the solution was stirred at 120° C. overnight. The reaction mixture was adjusted-to pH 2 with hydrochloric acid, extracted with ethyl acetate, washed with water and brine, and dried over anhydrous magnesium sulfate and the solvent was evaporated under reduced pressure. Methanesulfonic acid (50 ml) was added to the residue and the mixture was stirred at room temperature for 2 days. The reaction mixture was diluted with ethyl acetate, washed with water and brine, dried over anhydrous magnesium sulfate. The solvent was evaporated under reduced pressure. The residue was purified by silica gel column chromatography (eluting solvent; hexane:ethyl acetate=3:1) and recrystallized from ethyl acetate-hexane to give 5.3 g (90%) of plates of the indicated formula (5). Its mass spectrum showed a mass number of 286 ($M^+$).

EXAMPLE 9

Synthesis of 7,9-dihydroxy-10,11-dihydrodibenzo[b,f]thiepin-10-one [formula (6)]

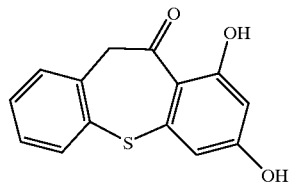

(6)

A mixture of pyridine hydrochloride (2.0 g) and 7,9-dimethoxy-10,11-dihydrodibenzo[b,f]thiepin-10-one (395 mg) was stirred at 195° C. for 1.5 hours and then ice water was added slowly. After extraction with ethyl acetate, the solution was successively washed with 1 N hydrochloric acid, water and brine. The organic layer was dried over anhydrous magnesium sulfate and concentrated. The residue was purified by silica gel column chromatography (eluting solvent; ethyl acetate:hexane=1:2) and recrystallized from diisopropyl ether-hexane to give 223 mg (61%) of plates of the indicated formula (6). The compound had a melting point of 248.1–250.0° C.

EXAMPLE 10

Synthesis of 10,11-dihydrodibenzo[b,f]thiepin-1,3-diol [formula (7)]

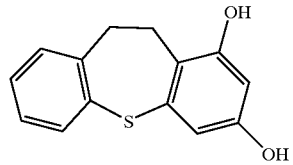

(7)

To a stirred suspension of 7,9-dimethoxy-10,11-dihydrodibenzo[b,f]thiepin-10-one (5.3 g)in methanol (25 ml) was added sodium borohydride (1.4 g) portionwise at 0° C. and the mixture was stirred at room temperature for 1 hour. To quench the reaction, dilute hydrochloric acid was added to the reaction mixture and then the methanol was evaporated under reduced pressure. The residue was diluted with ethyl acetate and the organic layer was successively washed with water and brine, dried over anhydrous magnesium sulfate and concentrated to dryness. To the resulting oil was added pyridine hydrochloride (30 g) and the mixture was stirred at 200° C. for 2 hours. The reaction mixture was partitioned between ethyl acetate and dilute hydrochloric acid. The organic layer was successively washed with water and brine, dried over anhydrous magnesium sulfate and concentrated. The residue was purified by silica gel column chromatography (eluting solvent; hexane:ethyl acetate=1:1). The resulting oil, dissolved in ethyl acetate (50 ml), was subjected to catalytic hydrogenation in the presence of platinum oxide (300 mg) at room temperature for 3 days. The reaction mixture was filtered and concentrated and the residue was purified by silica gel column chromatography (eluting solvent; hexane:ethyl acetate=2:1). Recrystallization from chloroform-hexane afforded 1.8 g (40%) of plates of the indicated formula (7). It had a melting point of 167.0–169.2° C.

Reference Example

Synthesis of 2-(3,5-dimethoxyphenylthio)benzoic acid [formula (10)]

A mixture of thiosalicylic acid (44 g), 5-chloro-1,3-dimethoxybenzene (49.2 g), potassium carbonate (78 g), copper (powder) (4.3 g) and copper(I) iodide (4.3 g) in N-methyl-2-pyrrolidone (390 ml) was stirred at 190° C. for 10 hours. The reaction mixture was treated by the same procedure as in Example 1 to give 8.0 g (10%) of a compound of the indicated formula (10).

INDUSTRIAL APPLICABILITY

The present invention provides a convenient process for efficient and massive production of diaryl sulfide derivatives useful as intermediates of medicines and the synthesis of intermediates for dibenzo[b,f]thiepines that has heretofore been possible only in a low yield in the prior art method can be markedly improved.

What is claimed is:

1. A process for producing a diaryl sulfide derivative or a salt thereof by reacting a halogen-substituted phenyl derivative of the general formula (1):

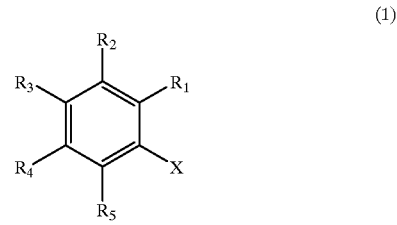

(1)

(where X is a halogen atom and $R_1$–$R_5$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group) with a disulfide derivative of the general formula (2):

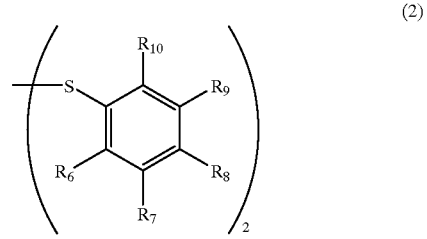

(2)

(where $R_6$–$R_{10}$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group) in the presence of a metal catalyst to form a sulfide bond, thereby producing a diaryl sulfide derivative of the general formula (3):

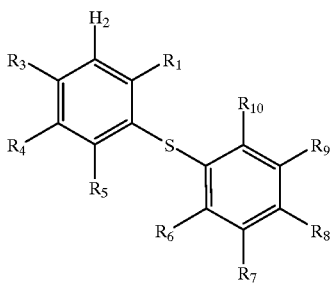

(3)

(where $R_1$–$R_{10}$ are the same as defined above).

2. The process for producing a diaryl sulfide derivative or a salt thereof according to claim 1, wherein the disulfide derivative of the general formula (2) is a compound that is produced by oxidizing a thiol derivative of the general formula (4):

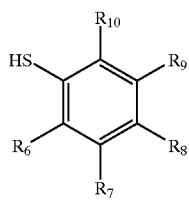

(4)

(where $R_6$–$R_{10}$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group).

3. The process for producing a diaryl sulfide derivative or a salt thereof according to claim 1, wherein the disulfide derivative of the general formula (2) is an intermediate that is produced within the reaction system starting from a thiol derivative of the general formula (4) as a starting material:

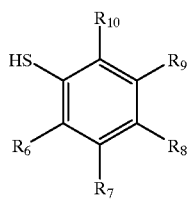

(4)

(where $R_6$–$R_{10}$ is any substituent selected from among hydrogen, a lower alkyl group, a lower cycloalkyl group, an aryl group, a halogen atom, a lower alkoxyl group, an amino group, an N-lower acylamino group, a nitro group, a lower alkylthio group and a carboxyl group).

4. The process for producing a diaryl sulfide derivative or a salt thereof according to claim 1, wherein the metal catalyst is a copper catalyst or a nickel catalyst.

5. The process for producing a diaryl sulfide derivative or a salt thereof according to claim 1 wherein the diaryl sulfide derivative or a salt thereof is an intermediate for a pharmaceutical compound.

6. The process for producing a diaryl sulfide derivative or a salt thereof according to claim 5, wherein said pharmaceutical compound is a dibenzo[b,f]thiepine derivative.

7. The process for producing a diaryl sulfide derivative or a salt thereof according to claim 6, which comprises the steps of:

reacting a 2-halobenzoic acid of the general formula (8):

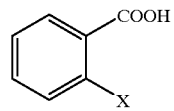

(8)

(where X is a halogen atom) with bis(3,5-dimethoxyphenyl)-disulfide of the formula (9):

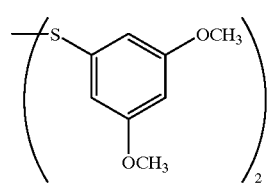

(9)

in the presence of a metal catalyst to form a sulfide bond, thereby producing 2-(3,5-dimethoxyphenylthio)benzoic acid of the formula (10):

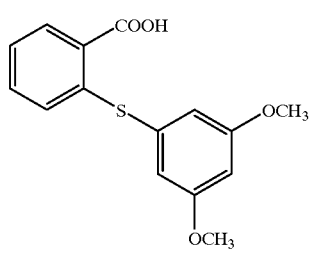

(10)

then reducing the compound (10) to form an alcohol derivative of the formula (11):

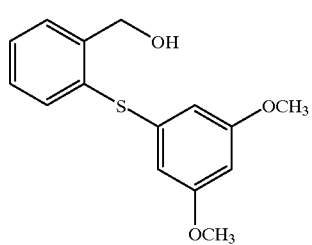

(11)

reacting the compound (11) with a halogenating agent or a pseudo-halogenating agent to produce a halogen derivative of the general formula (12):

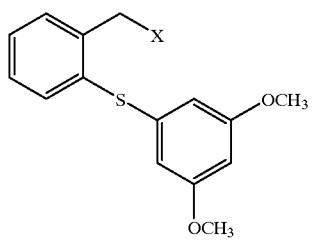
(12)

(where X is a halogen atom or a pseudo-halogen leaving group);

reacting the compound (12) with a nitrile forming agent to produce a nitrile derivative, or 2-(3,5-dimethoxyphenyl-thio)benzylnitrile of the formula (13):

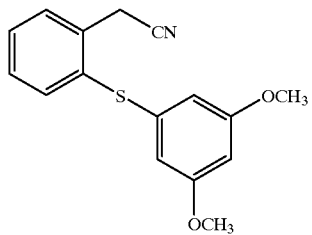
(13)

hydrolyzing the compound (13) to generate a carboxylic acid derivative; and cyclizing this derivative by an intramolecular Friedel-Crafts reaction to yield 7,9-dimethoxy-10,11-dihydrodibenzo-[b,f]thiepin-10-one of the formula (5):

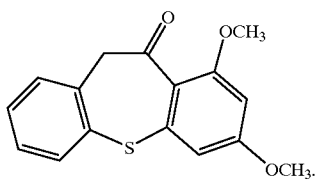
(5)

8. The process for producing a diaryl sulfide derivative or a salt thereof according to claim 7, wherein said 7,9-dimethoxy-10,11-dihydrodibenzo[b,f]thiepin-10-one is deprotected to yield a diol form, or 7,9-dihydroxy-10,11-dihydrodibenzo[b,f]thiepin-10-one of the formula (6):

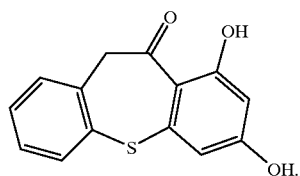
(6)

9. The process for producing a diaryl sulfide derivative or a salt thereof according to claim 8, wherein said diol compound 7,9-dihydroxy-10,11-dihydrodibenzo[b,f] thiepin-10-one or said dimethoxy compound 7,9-dimethoxy-10,11-dihydrodibenzo-[b,f]thiepin-10-one is reduced and deprotected to yield 10,11-dihydrodibenzo[b,f] thiepine-1,3-diol of the formula (7):

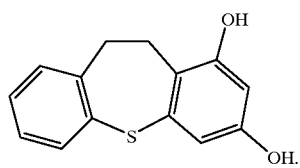
(7)

* * * * *

UNITED STATES PATENT AND TRADEMARK OFFICE
CERTIFICATE OF CORRECTION

PATENT NO.   : 6,207,837 B1
DATED        : March 27, 2001
INVENTOR(S)  : Naomi Ohtsuka et al.

It is certified that error appears in the above-identified patent and that said Letters Patent is hereby corrected as shown below:

<u>Title page,</u>
Item [57], ABSTRACT
Lines 4 and 25, replace "[b,f]" with -- [*b,f*] --
Line 16, counting each formula as a single line: replace "is" with -- are --

<u>Column 1,</u>
Lines 12, 23, 24, 28, 43, 50, 53 and 66, replace "[b,f]" with -- [*b,f*] --
Line 21, replace "dimethoxy-phenyl" with -- dimethoxyphenyl --

<u>Column 2,</u>
Line 34, replace "is" with -- are --
Line 58, replace "[b,f]" with -- [*b,f*] --

<u>Column 3,</u>
Line 12: replace "is" with -- are --
Lines 24, 27, 28, 29-30, 41 and 53, replace "[b,f]" with -- [*b,f*] --

<u>Column 4,</u>
Line 3, replace "[b,f]" with -- [*b,f*] --

<u>Column 5</u>
Line 36, replace "dihydrodibenzo-[b,f]thiepine" with -- dihydrodibenzo[*b,f*]thiepin --
Lines 50, 52 and 66, replace "[b,f]" with -- [*b,f*] --

<u>Column 6</u>
Lines 1, 3 and 67, replace "[b,f]" with -- [*b,f*] --
Line 35, replace "°C." with --°C--
Lines 50-51, replace "dibenzo[b,f]thiepin" with --dibenzo[*b,f*]thiepine--

<u>Column 7</u>
Lines 3, 6, 7, 45 and 52, replace "[b,f]" with -- [*b,f*] --

UNITED STATES PATENT AND TRADEMARK OFFICE
CERTIFICATE OF CORRECTION

PATENT NO.    : 6,207,837 B1
DATED         : March 27, 2001
INVENTOR(S)   : Naomi Ohtsuka et al.

It is certified that error appears in the above-identified patent and that said Letters Patent is hereby corrected as shown below:

Column 8
Lines 33 and 38, replace "°C." with -- °C --

Column 9
Lines 1, 17, 32, 44 and 65, replace "°C." with -- °C --

Column 10
Lines 17 and 41, replace "°C." with -- °C --
Line 66, replace "[b,f]" with -- [*b,f*] --

Column 11
Line 66, replace "dmethoxyphenylthio" with -- dimethoxyphenylthio --

Column 12
Lines 1, 35 and 58, replace "°C." with -- °C --
Line 19, replace "synthesis" with -- Synthesis --
Line 33, replace "Dimethoxyphenylthio" with -- dimethoxyphenylthio --
Line 59, replace "adjusted-to" with -- adjusted to --

Column 13
Lines 7, 20, 33 and 46, replace "[b,f]" with -- [*b,f*] --
Lines 21, 48 and 56, replace "°C." with -- °C --

Column 14
Line 12, replace "°C." with -- °C --
Line 23, replace "[b,f]" with -- [*b,f*] --
Line 61, counting each formula as a single line: replace "is" with -- are --

UNITED STATES PATENT AND TRADEMARK OFFICE
CERTIFICATE OF CORRECTION

PATENT NO. : 6,207,837 B1
DATED : March 27, 2001
INVENTOR(S) : Naomi Ohtsuka et al.

It is certified that error appears in the above-identified patent and that said Letters Patent is hereby corrected as shown below:

Column 15,
Lines 32 and 53, counting the formula as a single line: replace "is" with -- are --

Column 16,
Line 3, replace "[b,f]" with -- [*b,f*] --

Column 17,
Line 42, replace "dihydrodibenzo-[b,f]thiepin" with -- dihydrodibenzo[*b,f*]thiepin --

Column 18,
Lines 13, 15, 28 and 30, replace "[b,f]" with -- [*b,f*] --
Lines 31-32, replace "[b,f]thiepine" with -- [*b,f*]thiepin --

Signed and Sealed this

First Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,207,837 B1
DATED : March 27, 2001
INVENTOR(S) : Naomi Ohtsuka et al.

It is certified that error appears in the above-identified patent and that said Letters Patent is hereby corrected as shown below:

Title page,
Item [57], ABSTRACT
Lines 4 and 25, replace "[b,f]" with -- [*b,f*] --
Line 16, counting each formula as a single line: replace "is" with -- are --

Column 1,
Lines 12, 23, 24, 28, 43, 50, 53 and 66, replace "[b,f]" with -- [*b,f*] --
Line 21, replace "dimethoxy-phenyl" with -- dimethoxyphenyl --

Column 2,
Line 34: replace "is" with -- are --
Line 58: replace "[b,f]" with -- [*b,f*] --

Column 3,
Line 12: replace "is" with -- are --
Lines 24, 27, 28, 29-30, 41 and 53, replace "[b,f]" with -- [*b,f*] --

Column 4,
Line 3, replace "[b,f]" with -- [*b,f*] --

Column 5
Line 36, replace "dihydrodibenzo-[b,f]thiepine" with -- dihydrodibenzo[*b,f*]thiepin --
Lines 50, 52 and 66, replace "[b,f]" with -- [*b,f*] --

Column 6
Lines 1, 3 and 67, replace "[b,f]" with -- [*b,f*] --
Line 35, replace "°C." with --°C--
Lines 50-51, replace "dibenzo[b,f]thiepin" with --dibenzo[*b,f*]thiepine--

Column 7
Lines 3, 6, 7, 45 and 52, replace "[b,f]" with -- [*b,f*] --

UNITED STATES PATENT AND TRADEMARK OFFICE
CERTIFICATE OF CORRECTION

PATENT NO. : 6,207,837 B1
DATED : March 27, 2001
INVENTOR(S) : Naomi Ohtsuka et al.

It is certified that error appears in the above-identified patent and that said Letters Patent is hereby corrected as shown below:

Column 8
Lines 33 and 38, replace "°C." with -- °C --

Column 9
Lines 1, 17, 32, 44 and 65, replace "°C." with -- °C -

Column 10
Lines 17 and 41, replace "°C." with -- °C --
Line 66: replace "[b,f]" with -- [*b,f*] --

Column 11
Line 66, replace "dmethoxyphenylthio" with -- dimethoxyphenylthio --

Column 12
Lines 1, 35 and 58, replace "°C." with -- °C --
Line 19, replace "synthesis" with -- Synthesis --
Line 33, replace "Dimethoxyphenylthio" with -- dimethoxyphenylthio --
Line 59: replace "adjusted-to" with -- adjusted to --

Column 13
Lines 7, 20, 33 and 46, replace "[b,f]" with -- [*b,f*] --
Lines 21, 48 and 56, replace "°C." with -- °C --

Column 14
Line 12: replace "°C." with -- °C --
Line 23: replace "[b,f]" with -- [*b,f*] --
Line 61, counting each formula as a single line: replace "is" with -- are --

UNITED STATES PATENT AND TRADEMARK OFFICE
CERTIFICATE OF CORRECTION

PATENT NO. : 6,207,837 B1
DATED : March 27, 2001
INVENTOR(S) : Naomi Ohtsuka et al.

It is certified that error appears in the above-identified patent and that said Letters Patent is hereby corrected as shown below:

Column 15,
Lines 32 and 53, counting the formula as a single line: replace "is" with -- are --

Column 16,
Line 3, replace "[b,f]" with -- [*b,f*] --

Column 17,
Line 42, replace "dihydrodibenzo-[b,f]thiepin" with -- dihydrodibenzo[*b,f*]thiepin --

Column 18,
Lines 13, 15, 28 and 30, replace "[b,f]" with -- [*b,f*] --
Lines 31-32, replace "[b,f]thiepine" with -- [*b,f*]thiepin --

Signed and Sealed this

First Day of October, 2002

Attest:

Attesting Officer

JAMES E. ROGAN
*Director of the United States Patent and Trademark Office*